United States Patent [19]

Santini

[11] Patent Number: 4,859,679
[45] Date of Patent: Aug. 22, 1989

[54] ANTIULCER (ALKYLDITHIO) QUINOLINE DERIVATIVES

[75] Inventor: Conrad Santini, Groton, Conn.

[73] Assignee: Pfizer Inc., New York, N.Y.

[21] Appl. No.: 221,167

[22] Filed: Jul. 19, 1988

[51] Int. Cl.$^4$ .................. A61K 31/505; C07D 239/34; C07D 239/52; C07D 239/42
[52] U.S. Cl. ...................................... 514/273; 514/275; 544/300; 544/310; 544/315; 544/318; 544/319; 544/320; 544/321; 544/330; 544/298; 544/331
[58] Field of Search ............... 544/319, 320, 321, 330, 544/331, 298; 514/273

[56] References Cited

U.S. PATENT DOCUMENTS 4,673,677  6/1987  LaMattina ........................ 514/273
4,808,591  2/1989  Santini .............................. 514/274

FOREIGN PATENT DOCUMENTS 214479  3/1987  European Pat. Off. .
239129  9/1987  European Pat. Off. .

OTHER PUBLICATIONS

Clissold et al., Drugs 32: 15–47 (1986).

Primary Examiner—Cecilia Shen
Attorney, Agent, or Firm—Peter C. Richardson; J. Trevor Lumb; Robert K. Blackwood

[57] ABSTRACT

Quaternary 8-(alkyldithio)-1-(2-pyrimidyl)-quinolinium salts, inhibitors of the $H^{30}/K^+$ATPase enzyme, are useful in the treatment of ulcers.

12 Claims, No Drawings

ANTIULCER (ALKYLDITHIO) QUINOLINE DERIVATIVES

BACKGROUND OF THE INVENTION

The present invention relates to antiulcer agents and, in particular, to a series of quaternary 8-(alkyldithio)-1-(2-pyrimidyl)quinolinium salts which are inhibitors of the H+/K+ ATPase enzyme. The present invention also includes a method for treating peptic ulcers in mammals, including man; and a composition containing the therapeutic agents of this invention.

Chronic gastric and duodenal ulcers, together known as peptic ulcers, are a common ailment for which a variety of treatments, including dietary measures, drug therapy and surgery, are employed, depending on the severity of the condition. Particularly valuable therapeutic agents useful for the treatment of gastric hyperacidity and peptic ulcers are the histamine-H$_2$ receptor antagonists, which act to block the action of the physiologically active compound histamine at the H$_2$-receptor sites in the animal body and to thereby inhibit the secretion of gastric acid.

Various 2-(pyridylmethylsulfinyl)benzimidazoles, such as omeprazole, and related compounds (*Drugs,* 32, 15 (1986) are known to be antiulcer agents, acting by a mechanism involving inhibition of the H+/K+ ATPase enzyme system. More recently, such compounds have been reacted with alkyl mercaptans in the presence of an acid to form quaternary 2-(alkyldithio)-1-(2-benzimidazolyl)pyridinium salts, also found to be antiulcer agents with acid suppressing and cytoprotection properties; EP-214,479A. In addition, 8-(2-benzimidazolylsulfinylalkyl)-1,2-dihydro quinoline derivatives are reported in EP application 239,129A to possess such activity.

My copending U.S. patent application Ser. No. 07/156,371, filed Feb. 16, 1988, now U.S. Pat. No. 4,808,591, discloses antiulcer 8-(2-pyrimidylsulfinyl)-quinolines. The preparation of these compounds, which are employed as starting materials in the preparation of the compounds of the present invention, is fully disclosed in Preparations herein below.

SUMMARY OF THE INVENTION

The present invention is directed to compounds of the formula

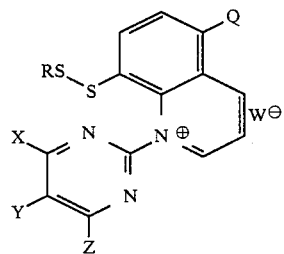

(I)

wherein
W$^\ominus$ is a pharmaceutically-acceptable anion;
R is (C$_1$-C$_5$)alkyl or benzyl;
Q is H, F, Cl, NO$_2$, (C$_1$-C$_5$)alkyl, CF$_3$, (C$_1$-C$_5$)alkoxy or (C$_2$-C$_4$)alkanoylamino;
X is H, (C$_1$-C$_5$)alkyl or (C$_1$-C$_5$)alkoxy;
Y is H, F, Cl, Br, (C$_1$-C$_5$)alkyl or (C$_1$-C$_5$)alkoxy; and
Z is H, (C$_1$-C$_5$)alkyl, (C$_5$-C$_7$)cycloalkyl, (C$_1$-C$_5$)alkoxy, (C$_5$-C$_7$)cycloalkoxy, phenoxy or benzyloxy.

The pharmaceutically acceptable anion, W$^\ominus$, can be, but is not limited to, such anions as Cl$^\ominus$, p-CH$_3$C$_6$H$_4$SO$_3^\ominus$, CH$_3$SO$_3^\ominus$, HSO$_4^\ominus$, (SO$_4$)$_{\frac{1}{2}}^\ominus$, H$_2$PO$_4^\ominus$, (HPO$_4$)$_{\frac{1}{2}}^\ominus$ and (cis-HOOCH=CHCOO)$^-$.

For reasons of facile preparation and good activity, the preferred value of W$^-$ is Cl$^-$; the preferred values of R are ethyl, isopropyl or t-butyl; and the preferred value of X is ethoxy, with Q, Y and Z as hydrogen.

The present invention is also directed to pharmaceutical compositions for inhibiting gastric parietal cell H+/K+ ATPase in a mammal which comprise a pharmaceutically acceptable carrier and a gastric parietal cell H+/K+ ATPase inhibiting amount of a compound of the formula (I), and to a method of treating gastric ulcers therewith.

DETAILED DESCRIPTION OF THE INVENTION

The present antiulcer compounds of formula (I) are readily prepared by reaction of the corresponding compound of the formula

(II)

wherein Q, X, Y and Z are as defined above with at least one molar equivalent each of a straight or branched chain (C$_1$-C$_5$)alkyl or benzyl mercaptan and an acid HW (where W forms a pharmaceutically-acceptable anion as defined above) in a reaction-inert solvent (suitably a partially aqueous solvent, preferably water and a lower alcohol such as ethanol). Temperature is not critical, for example, temperatures in the range of −10° C. to 60° C. being generally satisfactory. Since the reaction is rapid, ambient temperature is usually most convenient, with cooling, if desired, to avoid any possibility of an undue exotherm. The amount of acid is conveniently controlled by measurement of pH, a pH generally in the range of 1.5-2.5 usually providing the required amount of anion and affording a rapid rate of reaction. It will be evident that weaker acids which do not permit achieving a pH of 2.5 or lower are less preferred.

The sulfoxide starting materials are readily available by conventional m-chloroperbenzoic acid oxidation of the corresponding sulfides, which in turn are derived by reacting suitably substituted 2-halopyrimidine with a suitably substituted 8-mercaptoquinoline. The preparation of the required sulfoxides is extensively exemplified in Preparations below.

The utility of the present compounds as antiulcer agents is reflected in vitro by their inhibition of H+/K+ ATPase isolated from canine gastric mucosa. The enzyme activity was assayed according to Beil et al., *Brit. J. Pharmacol.* 82, 651–657 (1984) with slight modifications. The enzyme (1–2 micrograms) was preincubated at 37° C. for 45 minutes with a medium containing 2×10$^{-3}$M MgCl$_2$, 0.05M Tris-Cl buffer (pH 7.5) with or without 0.01M KCl, and the acid activated test drug in a final volume of 0.590 ml. The reaction was started by the addition of 0.010 mmol of ATP (final concentration $3 \times 10^{-3}$M). The reaction was terminated by adding trichloroacetic acid to a concentration of 4.2%. Liberated inorganic phosphate was determined using Fiske and Subbarow Reducer available commercially (e.g., from Sigma Chemical Co., P. O. Box 14508, St. Louis, MO 63178, U.S.A.). In this test the drugs are preferably first acid activated by incubating in 1:1 dimethylsulfoxide:0.02N HCl at 37° C. for 30 minutes.

The in vivo utility of the present compounds as antiulcer agents is also particularly shown by their cytoprotective activity. Such activity is demonstrated by the inhibition of ethanol-induced gastric ulceration in rats, using the method of Example 18 of U.S. Pat. No. 4,560,690.

For use in the treatment or prevention of ulcers in a mammal, including man, a compound of the formula (I) is administered in a parietal cell $H^+/K^+$ ATPase inhibiting amount of about 0.25–50 mg/kg/day, in single or divided daily doses. In particular cases, dosages outside that range are prescribed at the discretion of the attending physician. The preferred route of administration is generally oral, but parenteral administration (e.g. intramuscular, intravenous, intradermal) will be preferred in special cases, e.g., where oral absorption is impaired as by disease, or the patient is unable to swallow.

The compounds of the present invention are generally administered in the form of pharmaceutical compositions comprising at least one of the compounds of the formula (I), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; and, for parenteral administration, in the form of injectable solutions or suspensions, and the like.

The present invention is illustrated by the following examples, but is not limited to the details thereof.

EXAMPLE 1

8-(t-Butyldithio)-1-(4-ethoxy-2-pyrimidyl)quinolinium Chloride t-Butyl mercaptan (8 ml) was dissolved in 400 ml of 7:3 ethanol:water and the pH adjusted to 2 with 1N HCl. 8-(4-Ethoxy-2-pyrimidylsulfinyl)quinoline (600 mg) was added and the mixture stirred for 20 minutes, then stripped of solvent. The resulting residue was partitioned between 250 ml each of $CHCl_3$ and brine, and the organic layer separated, dried ($MgSO_4$), stripped to a second residue and chromatographed on silica gel using 1:49 ethanol:$CH_2Cl_2$ as eluant to yield 140 mg of title product, m.p. 129°–132° C. (after trituration with isopropyl ether); $^1$H-NMR ($CDCl_3$) delta (ppm) 8.11, d, 1H (J=6.6 Hz); 7.85, dd, 1H (J=7.4, 1.8 Hz); 7.13, m, 2H; 6.75 d, 1H (J=9.7 Hz); 6.56 bd, 1H (J=4.6 Hz); 6.20, m, 2H; 4.31, vbs, 2H; 4.05, pent, 1H (J=4.7 Hz); 3.87, pent, 1H (J=4.7 Hz); 1.30, bt, 3H (J=4.6 Hz); 1.18, t, 3H (J=7.1 Hz); 1.12, s, 9H).

EXAMPLE 2

8-(Isopropyldithio)-1-(4-ethoxy-2-pyrimidyl)-quinolinium Chloride

By the method of the preceding Example the same quinoline derivative (800 mg) and 10 ml of isopropyl mercaptan were converted to 208 mg of chromatographed title product isolated in the form of an oil; $^1$H-NMR ($CDCl_3$) delta (ppm) 8.09, d, 1H (J=5.6 Hz); 7.84 (dd, 1H (J=7.8, 1.3 Hz); 7.19, d, 1H (J=7.9 Hz); 7.15, vbs, 1H; 7.05, dd, 1H (J=7.4, 1.7 Hz); 6.58, d, 1H (J=9.2 Hz); 6.15, m, 2H; 4.34, vbs, 2H; 3.37, pent, 1H (J=6.8 Hz); 2.97, pent, 1H (J=6.8 Hz); 1.53, d, 3H (J=6.1 Hz); 1.30, vbt, 3H (J=6.4 Hz); 1.19, m, 6H.

EXAMPLE 3

8-(Ethyldithio)-1-(4-ethoxy-2-pyrimidyl)quinolinium Chloride

Ethyl mercaptan (10 ml) was dissolved in 500 ml of 7:3 ethanol:$H_2O$ at 0° C., and the pH adjusted to 2.0 with 1N HCl. 8-(4-Ethoxy-2-pyrimidylsulfinyl)quinoline (500 mg) was added and the mixture stirred for 4 hours at 0° C. To remove excess ethyl mercaptan, the reaction mixture was evaporated under a stream of nitrogen as the temperature was allowed to rise to room temperature, then stripped and the residue chromatographed as in Example 1 to yield 128 mg of title product; m.p. 86°–90° C. (following trituration with isopropyl ether); $^1$H-NMR ($CDCl_3$) delta (ppm) 8.07, d, 1H (J=5.5 Hz); 7.83, dd, 1H (J=8.0, 1.5 Hz); 7.19, d, 1H (J=8.0 Hz); 7.11 vbs, 1H; 7.07, dd, 1H (J=7.4, 1.8 Hz); 6.60, d, 1H (J=9.2 Hz); 6.17, d, 1H (J=5.6 Hz); 6.14, d, 1H (J=5.5 Hz); 4.30, vbs, 2H; 2.90, dt, 1H ($J_*$=7.1 Hz, $J_d$=5.2 Hz); 2.61, m, 3H; 1.32, t, 3H (J=7.2 Hz); 1.30, vbs, 3H; 1.15, t, 3H (J=7.4 Hz).

EXAMPLE 4

By the general method of Examples 1–3, the following additional 8-(alkyldithio)-1-(2-pyrimidyl)-quinolinium chlorides are prepared from the appropriate mercaptan and the corresponding 8-(2-pyrimidylsulfinyl)quinoline.

| Alkyl or Aralkyl Group | Pyrimidine Substituent(s) | 5-Quinoline Substituent |
| --- | --- | --- |
| methyl | none | none |
| ethyl | 4-propyloxy | none |
| propyl | 4-methoxy | none |
| isopropyl | 4-phenoxy | none |
| sec-butyl | 4-benzyloxy | none |
| isobutyl | 4,6-dimethoxy | none |
| pentyl | 4-amino | none |
| methyl | 4,6-dimethyl | none |
| ethyl | 4-ethoxy-6-methyl | none |
| propyl | 4-cyclohexyloxy | none |
| isopropyl | none | chloro |
| butyl | 4-methyl-6-pyrrolidino | none |
| isobutyl | 4-methyl | none |
| t-butyl | 4-ethyl-6-methyl | none |
| pentyl | none | nitro |
| 1-ethylpropyl | 4,6-dimethyl | nitro |
| methyl | 4-methyl | nitro |
| ethyl | 5-methyl-4-methoxy | none |
| isopropyl | none | fluoro |
| t-butyl | 4-methyl | acetamido |
| pentyl | 4,6-dimethyl | chloro |
| benzyl | 4-methoxy-6-methyl | none |
| methyl | 4-isopropoxy | none |
| butyl | 5-chloro | none |
| sec-butyl | 5-bromo | none |
| isobutyl | 4-methoxy | chloro |
| t-butyl | 4-ethoxy | chloro |
| 1-ethylpropyl | 4-methyl | fluoro |
| benzyl | 4-methoxy-6-methyl | chloro |
| ethyl | 4-ethoxy-5-methyl | none |
| propyl | 4-ethoxy-6-methyl | chloro |
| butyl | 4,6-dimethyl | fluoro |
| sec-butyl | 5-methyl | none |
| isobutyl | 4,6-dimethyl | acetamido |

PREPARATION 1

8-(2-Pyrimidylthio)quinoline

To a solution of 210 mg. (1.06 m mole) of quinoline-8-thiol hydrochloride in 5 ml. of dry methanol was added 128 mg. (1.05 mmol) of 2-chloropyrimidine in 2 ml. of the same solvent followed by 0.148 ml (1 mmol) of dry triethylamine. The reaction mixture was allowed to stir at room temperature overnight followed by the removal of the methanol in vacuo. The residue was partitioned between a saturated sodium bicarbonate solution and ethyl acetate. The organic phase was separated, dried and concentrated. The residue was redissolved in chloroform and concentrated without heat. The residue was triturated with ethyl acetate, filtered and dried, 170 mg., m.p. 165°–168° C.

PREPARATION 2

Employing the procedure of Preparation 1 and starting with the appropriate starting materials, the following sulfides were prepared:

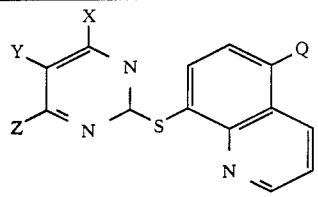

| X | Y | Z | Q |
|---|---|---|---|
| CH₃O | H | H | H |
| φO | H | H | H |
| C₂H₅O | H | H | H |
| φCH₂O | H | H | H |
| CH₃O | H | CH₃O | H |
| CH₃ | H | CH₃ | H |
| n-C₃H₇O | H | H | H |
| CH₃ | H | C₂H₅O | H |
| cyclohexyl-O | H | H | H |
| H | H | H | Cl |
| CH₃ | H | H | H |
| H | Cl | H | H |
| CH₃ | H | C₂H₅ | H |
| H | H | H | NO₂ |
| CH₃ | H | CH₃ | NO₂ |
| CH₃ | H | H | NO₂ |
| CH₃O | CH₃ | H | H |
| H | H | H | NHCOCH₃ |
| H | H | H | F |
| n-C₄H₉O | H | H | H |
| H | Br | H | H |
| CH₃ | H | H | Cl |
| CH₃ | H | H | NHCOCH₃ |
| CH₃ | H | CH₃ | Cl |
| CH₃ | H | CH₃O | H |
| i-C₃H₇O | H | H | H |
| CH₃O | H | H | Cl |
| C₂H₅O | H | H | Cl |
| CH₃ | H | H | F |
| CH₃ | H | CH₃ | Cl |
| C₂H₅O | CH₃ | H | H |
| C₂H₅O | H | CH₃ | Cl |
| CH₃ | H | CH₃ | F |
| H | CH₃ | H | H |

*-continued*

| X | Y | Z | Q |
|---|---|---|---|
| CH₃ | H | CH₃ | NHCOCH₃ |

PREPARATION 3

8-(2-Pyrimidylsulfinyl)quinoline

To a solution of 5 ml. of tetrahydrofuran containing 170 mg. (0.71 mmol) of 8-(2-pyrimidylthio)quinoline was added 300 mg. of sodium bicarbonate and the mixture cooled to 0° C. m-Chloroperbenzoic acid (85%, 153 mg., 1.0 molar equivalent) in 5 ml. of the same solvent was added dropwise. After the addition was complete the reaction was allowed to warm to 25° C. and was stirred overnight. The reaction mixture was poured into a sodium bicarbonate solution and the product extracted with ethyl acetate. The organic layer was separated, dried over sodium sulfate and concentrated in vacuo. The residue was triturated with a small amount of ethyl acetate and filtered to yield title product, 84 mg., m.p. 152°–155° C.

The NMR spectrum (300 MHz, CDCl₃) showed absorption at 8.86(dd, J=4.3, 1.6 Hz, 1H), 8.73(d, J=5.0 Hz, 2H), 8.48(dd, J=7.2, 1.2 Hz, 1 Hz), 8.18 (dd, J=8.1, 1.5 Hz, 1H), 7.95(dd, J=8.3, 1.3 Hz, 1H), 7.76(dd, J=9.0, 7.2 Hz, 1H), 7.43(dd, J=8.2, 4.3 Hz, 1H) and 7.24(t, J=5.1 Hz, 2H)ppm.

PREPARATION 4

8-(4-n-Propyloxy-2-pyrimidylsulfinyl)quinoline

To a mixture of 710 mg. (2.38 mmol) of 8-(4-propyloxy-2-pyrimidylthio)quinoline and 999 mg. of sodium bicarbonate (11.9 mmol) in 40 ml. of methylene chloride cooled to 0° C. was added dropwise over a period of 15 minutes 574 mg. (2.64 mmol) of 85% m-chloroperbenzoic acid in 15 ml. of the same solvent. The reaction mixture was stirred for 30 minutes and was then allowed to warm to room temperature and stirred overnight. The reaction was diluted with methylene chloride and the organic layer washed successively with a saturated sodium bicarbonate solution, water and a saturated brine solution. The organic phase was separated, dried over magnesium sulfate and concentrated to give 745 mg. of crude product which was purified by chromatographing on silica gel, 367 mg.

The NMR spectrum (300 MHz, CDCl₃) showed absorption at 8.85(dd, J=4.3, 1.6 Hz, 1H), 8.42(dd, J=7.2, 1.3 Hz, 1H), 8.38(d, J=5.5 Hz, 1H), 8.17(dd, J=8.1, 1.6 Hz, 1H), 7.92(dd, J=8.3, 1.4 Hz, 1H), 7.72(t, J=7.7 Hz, 1H), 7.4(dd, J=8.1, 4.0 Hz, 1H), 6.54(d, J=5.6 Hz, 1H), 4.0(m, 2H), 1.48(b, 2H) and 0.79(t, J=7.4 Hz, 3H)ppm.

PREPARATION 5

Employing the general oxidation procedures of Example 1 or 2 and starting with the appropriate sulfide the following products were prepared

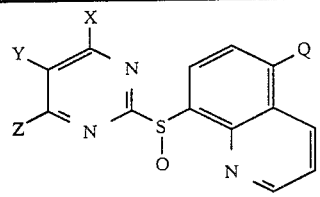

| X | Y | Z | Q | NMR(300 MHz, ppm) |
|---|---|---|---|---|
| CH₃O | H | H | H | (CDCl₃) 8.87(dd, J = 4.3, 2.3Hz, 1H), 8.45(dd, J = 7.2, 1.5Hz, 1H), 8.4(dd, J = 5.6, 1.1Hz, 1H), 8.19(dd, J = 8.8, 2.1Hz, 1H), 7.95(d, J = 8.3Hz, 1H), 7.75 (t, J = 7.2Hz, 1H), 7.43(dd, J = 8.4, 4.1Hz, 1H), 6.59(dd, J = 6.0, 1.1Hz, 1H), 3.73(s, 3H). |
| φO | H | H | H | (CDCl₃) 8.7(dd, J = 4.3, 1.7Hz, 1H), 8.59(d, J = 6.1Hz, 1H), 8.31(dd, J = 7.2, 1.3Hz, 1H), 8.15(dd, J = 8.1, 1.6Hz, 1H), 7.9(dd, J = 8.3, 1.3Hz, 1H), 7.66(dd, J = 9.0, 7.7Hz, 1H), 7.38(dd, J = 8.1, 4.3Hz, 1H), 7.13(m, 3H), 6.74(d, J = 5.5Hz, 1H), 6.7(m, 2H). |
| C₂H₅O | H | H | H | (CDCl₃) 8.85(dd, J = 4.3, 1.7Hz, 1H), 8.42(d, J = 5.3Hz, 1H), 8.38(d, J = 5.5Hz, 1H), 8.17(dd, J = 8.8, 1.7Hz, 1H), 7.92(bd, J = 8.3Hz, 1H), 7.72(t, J = 7.2Hz, 1H), 7.42(dd, J = 8.8, 4.4Hz, 1H), 6.54(d, J = 5.5Hz, 1H), 4.13(dq, J = 6.8, 1.5Hz, 2H), 1.07(t, J = 6.8Hz, 3H). |
| φCH₂O | H | H | H | (CDCl₃) 8.86(dd, J = 4.3, 1.9Hz, 1H), 8.46(m, 2H), 8.2(dd, J = 8.5, 1.8Hz, 1H), 7.95(dd, J = 8.3, 1.3Hz, 1H), 7.75(t, J = 7.8Hz, 1H), 7.43(dd, J = 8.1, 4.3Hz, 1H), 7.23–7.26(m, 3H), 7.14–7.17(m, 2H), 6.63(d, J = 5.5Hz, 1H), 5.16(AB, J = 12.2Hz, 2H). |
| CH₃O | H | CH₃O | H | (CDCl₃) 8.97(dd, J = 4.3, 1.6Hz, 1H), 8.28(dd, J = 7.2, 1.3Hz, 1H), 8.2(dd, J = 8.1, 1.6Hz, 1H), 7.94(dd, J = 7.7, 1.3Hz, 1H), 7.7(t, J = 7.8Hz, 1H), 7.48(dd, J = 8.3, 4.1Hz, 1H),7.07 (s, 1H), 3.92(s, 3H), 3.66(s, 3H). |
| CH₃ | H | CH₃ | H | (CDCl₃) 8.87(dd, J = 4.3, 1.9Hz, 1H), 8.44(dd, J = 7.2, 1.9Hz, 1H), 8.16(dd, J = 8.2, 1.6Hz, 1H), 7.91(dd, J = 8.0, 1.6Hz, 1H), 7.73(t, J = 7.8Hz, 1H), 7.41(dd, J = 8.1, 4.3Hz, 1H), 6.9(s, 1H), 2.40(s, 6H). |
| C₂H₅O | H | CH₃ | H | (CDCl₃) 8.86(dd, J = 4.2, 1.9Hz, 1H), 8.42(d, J = 7.3Hz, 1H), 8.18(bd, J = 8.2Hz, 1H), 7.92(d, J = 7.7Hz, 1H), 7.73(t, J = 7.8Hz, 1H),7.42(dd, J = 8.2, 4.1Hz, 1H), 6.37(s, 1H), 4.0(bq, J = 7.0Hz, 2H), 2.43(s, 3H), .97(t, J = 7.1Hz, 3H). |
| cyclohexyl-O | H | H | H | (CDCl₃) 8.85(dd, J = 4.3, 1.7Hz, 1H) 8.43(m, 2H), 8.19(dd, J = 8.2, 1.7Hz, 1H), 7.94(bd, J = 7.2Hz, 1H), 7.75(t, J = 7.1Hz, 1H), 7.43(dd, J = 8.2, 4.3Hz, 1H), 6.51(d, J = 6.2Hz, 1H), 4.63(bq, 1H), 1.35–1.6(m, 7H), 1.08–1.2(m, 3H). |
| H | H | H | Cl | (CDCl₃) 8.88(dd, J = 4.3, 1.7Hz, 1H), 8.73(dd, J = 5.0, 1.3Hz, 2H), 8.57(dd, J = 8.3, 1.2Hz, 1H), 8.4(d, J = 7.9Hz, 1H), 7.85(d, J = 7.9Hz, 1H), 7.53(dd, J = 8.4, 4.2Hz, 1H), 7.25(t, J = 5.0Hz, 1H). |
| CH₃ | H | H | H | (CDCl₃) 8.86(dd, J = 4.3, 1.6Hz, 1H), 8.5(d, J = 4.8Hz, 1H), 8.46(dd, J = 7.2, 1.3Hz, 1H), 8.17(dd, J = 8.8, 1.6Hz, 1H), 7.93(dd, J = 8.3, 1.3Hz, 1H), 7.75(t, J = 7.8Hz, 1H), 7.41(dd, J = 8.2, 4.3Hz, 1H), 7.06(d, J = 4.9Hz, 1H), 2.51(s, 3H). |
| C₂H₅ | H | CH₃ | H | (DMSO—d₆) 8.76(dd, J = 4.0, 1.4Hz, 1H), |

-continued

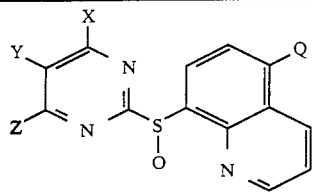

| X | Y | Z | Q | NMR(300 MHz, ppm) |
|---|---|---|---|---|
| | | | | 8.47(dd, J = 8.5, 1.5Hz, 1H), 8.22(dd, J = 7.3, 1.4Hz, 1H), 8.18(dd, J = 7.9, 1.2Hz, 1H), 7.88(t, J = 7.8Hz, 1H), 7.56(dd, J = 8.1, 4.2Hz, 1H), 7.28(s, 1H), 2.56(q, J = 7.5Hz, 2H), 2.36(s, 3H), .91(t, J = 7.6Hz, 3H). |
| H | H | H | NO$_2$ | (DMSO—d$_6$) 8.84(m, 4H), 8.74(d, J = 7Hz, 1H), 8.42(d, J = 7Hz, 1H), 7.8(dd, J = 7,4Hz, 1H), 7.6(t, J = 8Hz, 1H). |
| CH$_3$ | H | CH$_3$ | NO$_2$ | (DMSO—d$_6$) 8.82(m, 2H), 8.64(d, J = 7Hz, 1H), 8.34(d, J = 7Hz, 1H), 7.78(dd, J = 7,4Hz, 1H), 7.28(s, 1H), 2.3(s, 6H). |
| CH$_3$ | H | H | NO$_2$ | (CDCl$_3$) 8.92(dd, J = 4,2Hz, 1H), 8.86(d, J = 7Hz, 1H), 8.52(s, 2H), 8.42(d, J = 7Hz, 1H), 7.6(dd, J = 7,4Hz, 1H), 7.06(d, J = 7Hz, 1H), 2.3(s, 3H). |
| CH$_3$O | CH$_3$ | H | H | (CDCl$_3$) 8.84(dd, J = 4,2Hz, 1H), 8.42(dd, J = 7,2Hz, 1H), 8.19(s, 1H), 8.15(dd, J = 8, 1Hz, 1H), 7.91(dd, J = 8,1Hz, 1H), 7.71(t, J = 8Hz, 1H), 7.4(dd, J = 7,4Hz, 1H), 3.72(s, 3H), 2.02(s, 3H). |
| H | H | H | F | (DMSO—d$_6$) 8.8(m, 2H), 8.5(d, J = 7Hz, 1H), 8.2(m, 1H), 7.72(m, 2H), 7.64(dd, J = 7,4Hz, 1H), 7.54(t, J = 7Hz, 1H). |
| CH$_3$ | H | H | $\underset{\text{CH}_3\text{CNH}}{\overset{\text{O}}{\|}}$ | (DMSO—d$_6$) 10.27(s, 1H), 8.77(dd, J = 4, 1Hz, 1H), 8.64(d, J = 9Hz, 1H), 8.63(d, J = 5Hz, 1H), 8.17(d, J = 4Hz, 2H), 7.61(dd, J = 9,4Hz, 1H), 7.44(d, J = 5Hz, 1H), 2.48(s, 2H), 2.24(s, 3H). |
| CH$_3$O | H | CH$_3$ | H | (CDCl$_3$) 8.87 (dd, J = 4.3, 1.6Hz, 1H), 8.43(dd, J = 7.2, 1.3Hz, 1H), 8.18(dd, J = 8.4, 1.9Hz, 1H), 7.93(dd, J = 8.3, 1.3Hz, 1H), 7.73(t, J = 7.8Hz, 1H), 7.42(dd, J = 8.4, 4.3Hz, 1H), 6.4(s, 1H), 3.58(s, 3H), 2.42(s, 3H). |
| i-C$_3$H$_7$O | H | H | H | (CDCl$_3$) 8.87(dd, J = 4.3, 1.7Hz, 1H), 8.43(dd, J = 7.3, 1.4Hz, 1H), 8.4(d, J = 6.0Hz, 1H), 8.19(dd, J = 8.5, 1.5Hz, 1H), 7.93(d, J = 8.4Hz, 1H), 7.74(t, J = 7.4Hz, 1H), 7.43(dd, J = 8.6, 4.3Hz, 1H), 4.99(Sep, J = 6.0Hz, 1H), 1.01(d, J = 6.1Hz, 3H), .98(d, J = 6.1Hz, 3H). |
| H | Cl | H | H | (DMSO—d$^6$) 8.75(dd, J = 4, 2Hz, 1H), 8.47(dd, J = 8, 2Hz, 1H), 8.25(d, J = 7Hz, 1H), 8.22(d, J = 7Hz, 1H), 7.89(t, J = 8Hz, 1H), 7.83(s, 2H), 7.44(dd, J = 4, 2Hz, 1H). |
| H | Br | H | H | (DMSO—d$^6$) 8.74(dd, J = 4, 2Hz, 1H), 8.47(dd, J = 8, 2Hz, 1H), 8.24(d, J = 7Hz, 1H), 8.20(d, J = 7Hz, 1H), 7.89(t, J = 8Hz, 1H), 7.83(s, 2H), 7.56(dd, J = 4, 2Hz, 1H). |
| CH$_3$O | H | H | Cl | (CDCl$_3$) 8.89(dd, J = 4.3, 1.7Hz, 1H), 8.57(dd, J = 8.6, 1.7Hz, 1H), 8.38(d, J = 5.5Hz, 1H), 8.37(d, J = 7.9Hz, 1H), 7.83(d, J = 7.9Hz, 1H), 7.53(dd, J = 8.8, 4.3Hz, 1H), 6.60(d, J = 5.5Hz, 1H), 3.76(s, 3H). |
| C$_2$H$_5$O | H | H | Cl | (CDCl$_3$) 8.89(dd, J = 4.1, 1.4Hz, 1H), 8.56(dd, J = 8.8, 2.0Hz, 1H), 8.38(d, J = 5.7Hz, 1H), 8.36(d, J = 8.0Hz, 1H), 7.82(d, J = 7.9Hz, 1H), 7.53(dd, J = 8.6, 4.2Hz, 1H), 6.56(d, J = 5.6Hz, 1H), 4.17(quart., J = 7.0Hz, 2H), 1.12(t, J = 7.1Hz, 3H). |
| CH$_3$ | H | H | F | (DMSO—d$^6$) 8.85(d, J = 4Hz, 1H), 8.62(d, J = 5Hz, 1H), 8.56(d, J = 9Hz, 1H), 8.22(dd, J = 8, 6Hz, 1H), 7.74(dd, J = 10, 8Hz, 1H), 7.67(dd, J = 9, 4Hz, 1H), 7.44(d, |

-continued

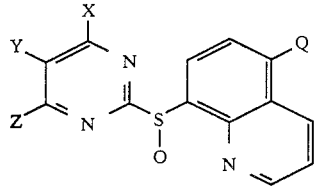

| X | Y | Z | Q | NMR(300 MHz, ppm) |
|---|---|---|---|---|
| | | | | J = 5Hz, 1H), 2.46(s, 3H). |
| $CH_3O$ | H | $CH_3$ | Cl | (DMSO—$d^6$) 8.91(dd, J = 4.3, 1.7Hz, 1H), 8.64(dd, J = 8.8, 1.5Hz, 1H), 8.20(d, J = 7.9Hz, 1H), 8.08(d, J = 7.9Hz, 1H), 7.75(dd, J = 8.7, 4.3Hz, 1H), 6.83(s, 1H), 3.52(s, 3H), 2.35(s, 3H). |
| $C_2H_5O$ | $CH_3$ | H | H | (DMSO—$d^6$) 8.86(dd, J = 4, 2Hz, 1H), 8.43(dd, J = 7, 2Hz, 1H), 8.22(s, 1H), 8.17 (dd, J = 9, 2Hz, 1H), 7.91(dd, J = 8, 2Hz, 1H), 7.73(t, J = 8Hz, 1H), 7.41(dd, J = 9, 4Hz, 1H), 4.15(quart., J = 7Hz, 2H), 2.02(s, 3H), 1.07(t, J = 7Hz, 3H). |
| $C_2H_5O$ | H | $CH_3$ | Cl | (DMSO—$d^6$) 8.91(dd, J = 4.1, 1.4Hz, 1H), 8.64(dd, J = 8.8, 1.4Hz, 1H), 8.20(d, J = 7.9Hz, 1H), 8.09(d, J = 7.9Hz, 1H), 7.75(dd, J = 8.8, 4.2Hz, 1H), 6.79(s, 1H), 3.90(quart., J = 7.0Hz, 2H), 2.37(s, 3H), 0.85(t, J = 6.9Hz, 3H). |
| $CH_3$ | H | $CH_3$ | F | (DMSO—$d^6$) 8.87(d, J = 5Hz, 1H), 8.56(d, J = 8Hz, 1H), 8.20(dd, J = 9, 6Hz, 1H), 7.74(dd, J = 10, 9Hz, 1H), 7.68(dd, J = 8, 5Hz, 1H), 7.30(s, 1H), 2.33(s, 6H). |
| H | $CH_3$ | H | H | (DMSO—$d^6$) 8.73(dd, J = 4, 2Hz, 1H), 8.67(s, 2H), 8.46(dd, J = 8, 2Hz, 1H), 8.25(d, J = 8Hz, 1H), 8.19(d, J = 9Hz, 1H), 7.90(t, J = 8Hz, 1H), 7.56(dd, J = 9, 4Hz, 1H), 2.23(s, 3H). |
| $CH_3$ | H | $CH_3$ | $\underset{CH_3CNH}{\overset{O}{\parallel}}$ | (DMSO—$d^6$) 10.24(s, 1H), 8.79(dd, J = 4, 1Hz, 1H), 8.63(dd, J = 9, 1Hz, 1H), 8.16(d, J = 2Hz, 1H), 7.59(dd, J = 9, 4Hz, 1H), 7.28(s, 1H), 2.34(s, 1H), 2.22 (s, 3H). |

I claim:

1. A compound of the formula

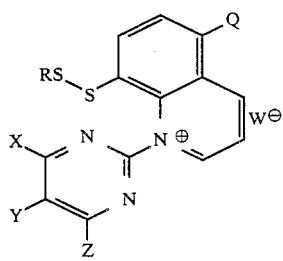

wherein $W^\ominus$ is a pharmaceutically-acceptable anion;

R is $(C_1-C_5)$alkyl or benzyl;

Q is H, F, Cl, $NO_2$, $(C_1-C_5)$alkyl, $CF_3$, $(C_1-C_5)$alkoxy or $(C_2-C_4)$alkanoylamino;

X is H, $(C_1-C_5)$alkyl or $(C_1-C_5)$alkoxy;

Y is H, F, Cl, Br, $(C_1-C_5)$alkyl or $(C_1-C_5)$alkoxy; and

Z is H, $(C_1-C_5)$alkyl, $(C_5-C_7)$cycloalkyl, $(C_1-C_5)$alkoxy, $(C_5-C_7)$cycloalkoxy, phenoxy or benzyloxy.

2. A compound of claim 1 wherein $W^\ominus$ is $Cl^\ominus$.

3. A compound of claim 1 wherein R is ethyl, isopropyl or t-butyl.

4. A compound of claim 3 wherein $W^\ominus$ is $Cl^\ominus$.

5. A compound of claim 1 wherein Q, Y and Z are hydrogen and X is ethoxy.

6. A compound of claim 5 wherein $W^\ominus$ is $Cl^\ominus$.

7. A compound of claim 5 wherein R is ethyl, isopropyl or t-butyl.

8. The compound of claim 6 wherein R is ethyl.

9. The compound of claim 6 wherein R is isopropyl.

10. The compound of claim 6 wherein R is t-butyl.

11. A pharmaceutical composition for inhibiting gastric parietal cell $H^+/K^+$ ATPase in a mammal which comprises a pharmaceutically acceptable carrier and a gastric parietal cell $H^+/K^+$ ATPase inhibiting amount of a compound according to claim 1.

12. A method of treating gastric ulcers by inhibiting parietal cell $H^+/K^+$ ATPase in a mammalian subject in need of such treatment which comprises administering to said subject a parietal cell $H^+/K^+$ ATPase inhibiting amount of a compound according to claim 1.

* * * * *